US009851296B2

(12) United States Patent
Partridge, Jr. et al.

(10) Patent No.: US 9,851,296 B2
(45) Date of Patent: Dec. 26, 2017

(54) DIAGNOSTIC SYSTEM FOR MEASURING TEMPERATURE, PRESSURE, $CO_2$ CONCENTRATION AND $H_2O$ CONCENTRATION IN A FLUID STREAM

(71) Applicant: UT-Battelle, LLC, Oak Ridge, TN (US)

(72) Inventors: William P. Partridge, Jr., Oak Ridge, TN (US); Gurneesh Singh Jatana, Knoxville, TN (US); Ji Hyung Yoo, East Amherst, NY (US); James E. Parks, II, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 15/355,762

(22) Filed: Nov. 18, 2016

(65) Prior Publication Data

US 2017/0074787 A1    Mar. 16, 2017

Related U.S. Application Data

(62) Division of application No. 14/831,913, filed on Aug. 21, 2015, now Pat. No. 9,541,498.

(51) Int. Cl.
*G01N 21/3504*    (2014.01)
*G01N 21/85*      (2006.01)
*G01N 33/00*      (2006.01)

(52) U.S. Cl.
CPC ..... *G01N 21/3504* (2013.01); *G01N 21/8507* (2013.01); *G01N 33/004* (2013.01);
(Continued)

(58) Field of Classification Search
CPC .. G01N 21/39; G01N 21/359; G01N 21/3504; G01N 2021/6484; G01N 2021/4742; G01N 33/004; G01N 33/0036
See application file for complete search history.

(56) References Cited

U.S. PATENT DOCUMENTS 4,800,886 A * 1/1989 Nestor ................ A61B 5/1459
                                                356/437
5,911,953 A * 6/1999 Ogata ................ G01N 21/3563
                                                250/343

(Continued)

OTHER PUBLICATIONS

Jatana, Gurneesh, S., "High-Speed Diode Laser Measurements of Temperature and Water Vapor Concentration in the Intake Manifold of Diesel Engine", International Journal of Engine Research, 2014 15:773 originally published online Jan. 30, 2014, http://jer.sagepub.com/content/15/7/773.

(Continued)

*Primary Examiner* — Marcus Taningco
(74) *Attorney, Agent, or Firm* — Colin L. Cini (57) ABSTRACT

A diagnostic system for measuring temperature, pressure, $CO_2$ concentration and $H_2O$ concentration in a fluid stream is described. The system may include one or more probes that sample the fluid stream spatially, temporally and over ranges of pressure and temperature. Laser light sources are directed down pitch optical cables, through a lens and to a mirror, where the light sources are reflected back, through the lens to catch optical cables. The light travels through the catch optical cables to detectors, which provide electrical signals to a processer. The processer utilizes the signals to calculate $CO_2$ concentration based on the temperatures derived from $H_2O$ vapor concentration. A probe for sampling $CO_2$ and $H_2O$ vapor concentrations is also disclosed. Various mechanical features interact together to ensure the pitch and catch optical cables are properly aligned with the lens during assembly and use.

3 Claims, 11 Drawing Sheets

(52) U.S. Cl.
CPC ............... *G01N 2021/8521* (2013.01); *G01N 2201/0638* (2013.01); *G01N 2201/06113* (2013.01)

(56) References Cited

U.S. PATENT DOCUMENTS

| | | |
|---|---|---|
| 7,839,492 B2 | 11/2010 | Parks, II |
| 9,000,374 B2 | 4/2015 | Parks, II et al. |
| 9,068,933 B2 | 6/2015 | Parks, II et al. |
| 2002/0158202 A1 | 10/2002 | Webber |
| 2009/0229250 A1* | 9/2009 | Yamakage ......... G01N 15/0205 60/276 |

OTHER PUBLICATIONS

Jatana, Gurneesh S., "Simultaneous High-Speed Gas Property Measurements at the Exhaust Gas Recirculation Cooler Exit and at the Turbocharger Inlet of a Multicylinder Diesel Engine Using Diode-Laser-Absorption Spectroscopy", Applied Optics, 2015, vol. 54, No. 5, pp. 1220-1231.

Jatana, Gurneesh S., "Development & Use of a Multiplexed Two-Color Sensor for Mapping EGR & Back-flowing Combustion Residual in the Intake Manifold of a Heavy Duty Diesel Engine", Powerpoint Presentation, 9th U.S. National Combustion Meeting, 2015, Cincinnati, Ohio.

* cited by examiner

DIAGNOSTIC SYSTEM FOR MEASURING TEMPERATURE, PRESSURE, $CO_2$ CONCENTRATION AND $H_2O$ CONCENTRATION IN A FLUID STREAM

CROSS REFERENCE TO RELATED APPLICATIONS

This application is a divisional application of copending U.S. patent application Ser. No. 14/831,913, entitled, "A DIAGNOSTIC SYSTEM FOR MEASURING TEMPERATURE, PRESSURE, CO2 CONCENTRATION AND H2O CONCENTRATION IN A FLUID STREAM", filed on Aug. 21, 2015, which claims the benefit of priority under 35 U.S.C. §120 to U.S. provisional patent application Ser. No. 62/162,934, entitled, "A DIAGNOSTIC SYSTEM FOR MEASURING TEMPERATURE, PRESSURE, CO2 CONCENTRATION AND H2O CONCENTRATION IN A FLUID STREAM", filed on May 18, 2015, and each is incorporated herein by reference. This application relates to U.S. application Ser. No. 14/051,788, entitled "EGR DISTRIBUTION AND FLUCTUATION PROBE BASED ON CO2 MEASUREMENTS", filed Oct. 11, 2013, now U.S. Pat. No. 9,068,933, by Parks et al, which is a Continuation-in-part of U.S. application Ser. No. 13/912,462, entitled "EGR DISTRIBUTION AND FLUCTUATION PROBE BASED ON CO2 MEASUREMENTS", filed Jun. 7, 2013, now U.S. Pat. No. 9,000,374, by Parks et al, which claims priority to U.S. Provisional Application Ser. No. 61/657,205, and each is incorporated herein by reference.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND

The present subject matter relates to internal combustion engine diagnostics and more specifically to apparatuses and methods for determining the spatial and temporal nonuniformities of $CO_2$ in a complex fluid stream. A complex fluid stream may contain concentrations of $CO_2$ that vary with space, time and temperature.

Internal combustion engines typically suffer from the production of undesirable $NO_x$ emissions. Experience has revealed that more $NO_x$ emissions are formed at higher combustion temperatures and that $NO_x$ formation has a nonlinear dependence on temperature. More specifically, lowering the combustion temperature by small amounts can result in relatively large reductions in $NO_x$ formation and is favorable in that respect.

Exhaust-gas recirculation, EGR, is a known technology used to reduce automotive $NO_x$ emissions, and involves mixing some of the engine exhaust gas products with the intake air stream before it enters the combustion chamber. The exhaust products act as a diluent in the inlet air that reduces peak combustion temperature. Ideally, the air/exhaust mixture, or EGR fraction, is uniform across the various cylinders of a multi-cylinder engine. However, practically, the EGR fraction can vary from cylinder to cylinder and cycle to cycle due to various spatial and temporal nonuniformities; e.g., non-ideal mixing characteristics, intake-manifold restrictions and path length differences, and overlap of valve timing events with manifold resonating. The actual combustion chamber charge is affected by: external EGR, residual backflow caused by valve overlap, and residual exhaust remaining in the combustion chamber between the piston and the cylinder head. Such nonuniformities can cause one cylinder to reach a limit (e.g., incomplete combustion, etc.) earlier than the other cylinders, and can limit the performance of the other cylinders. Ultimately, the result is lost efficiency and increased engine emissions.

Application Ser. No. 14/051,788, entitled EGR DISTRIBUTION AND FLUCTUATION PROBE BASED ON CO2 MEASUREMENTS describes an apparatus and method of determining spatial and temporal nonuniformities of $CO_2$ in an intake stream.

Figure 1:
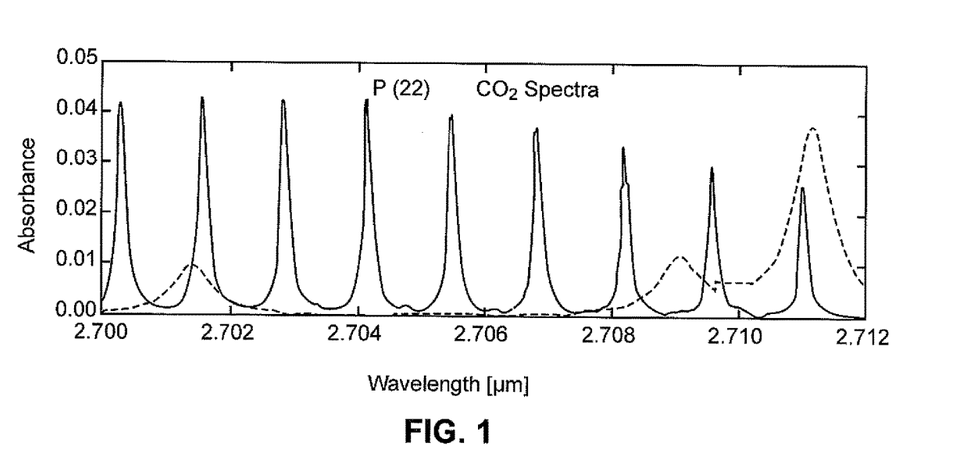
FIG. 1 is a graph of absorption as a function of $CO_2$ concentration and temperature.
Figure 2:
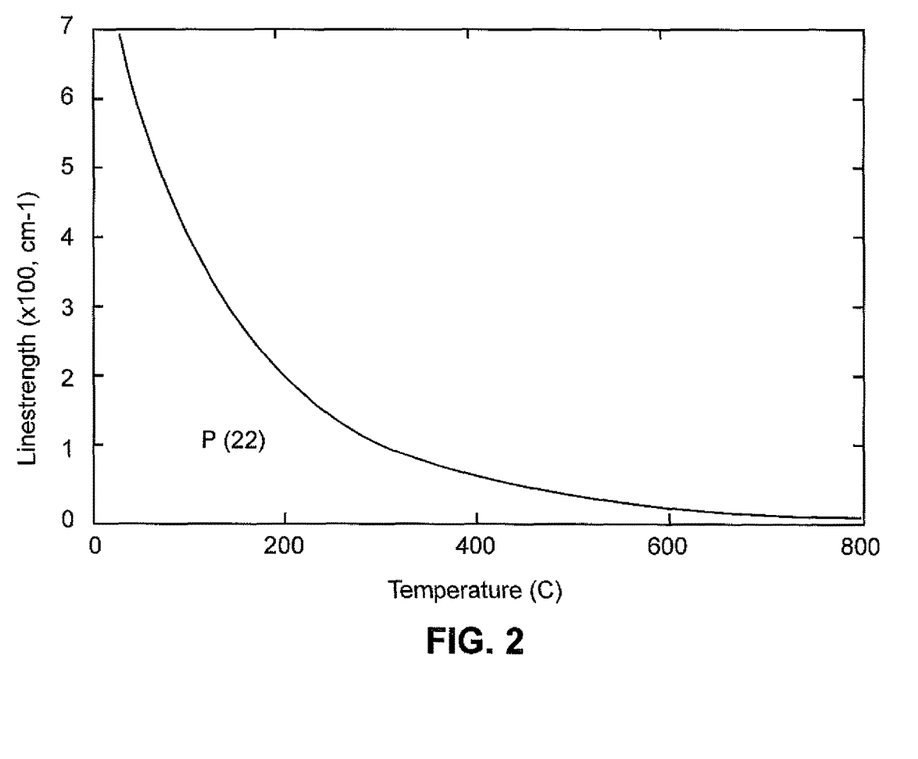
FIG. 2 is a graph of absorption line strength as a function of temperature with an indication of lower line strength at higher temperatures.
Figure 3:
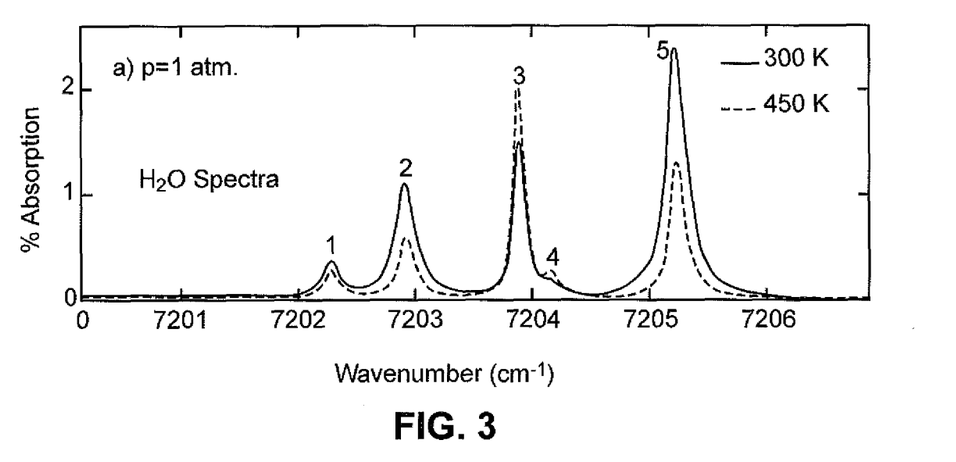
FIG. 3 is a graph of theoretical $H_2O$ absorption profile across a 6-cm-long absorption path.

$CO_2$ absorption spectra are affected by the temperature of the intake fluid stream itself. Since the backflow exhaust portion will be at a higher temperature than the external EGR, temperature correction is necessary to ensure $CO_2$ measurement is not underestimated at higher temperatures. See FIG. 1-3 for an illustration of these known phenomena.

Water vapor concentration may be used to determine intake charge temperature in the regions of $CO_2$ measurements for correction and more accurate measurements.

Jatana G S, Naik S V, Shaver G M, Lucht R P. "High-speed diode laser measurements of temperature and water vapor concentration in the intake manifold of a diesel engine." International Journal of Engine Research October 2014 vol. 15 no. 7 773-788 describes the use of a diode laser and absorption spectroscopy to determine the concentration of water vapor in an intake stream.

Jatana G S, Magee M, Fain D, Sameer V, Shaver G M, Lucht R P. "Simultaneous high-speed gas property measurements at the exhaust gas recirculation cooler exit and at the turbocharger inlet of a multicylinder diesel engine using diode-laser-absorption spectroscopy." Applied Optics, vol. 54, issue 5, p. 1220 describes the use of a diode laser and absorption spectroscopy to determine temperature, pressure and $H_2O$ vapor concentrations. See FIG. 3 for an example of known $H_2O$ vapor concentration spectra at two temperatures.

What is needed is an apparatus and method for measuring spatial and temporal $CO_2$ concentrations in a complex fluid stream that includes relatively cool external EGR and relatively hot backflow exhaust species present.

SUMMARY

The present disclosure provides a probe capable of providing rapid and accurate measurement of $CO_2$ concentrations in a complex fluid stream, such as an engine intake manifold, intake runner, exhaust gas recycling system or an engine exhaust gas manifold for example.

In one exemplary embodiment, a system for determining the concentration of $CO_2$ in a complex fluid stream is disclosed. A first laser light source is coupled to a first end of a first pitch optic cable. The first laser light source is a swept-λ laser configured to produce light output over a sweep range that includes a region having a significant absorption feature of $CO_2$ and at least one region of substantially zero absorption. A second laser light source is coupled to a first end of a second pitch optic cable. The second laser light source is configured to produce light output that includes a region having a significant absorption feature of $H_2O$. A lens is disposed proximate to a second end of each of the first and the second pitch optic cables for directing the first and second lights through a sampling chamber to a mirror. A first catch optic cable has a second end disposed proximate the lens for receiving light output from the first laser light source that is reflected from the mirror. A second catch optic cable has a second end disposed proximate the lens for receiving light output from the second laser light source that is reflected from the mirror. A first detector is affixed to a first end of the first catch optic cable, the first detector provides a first output signal that is representative of light intensity across the sweep range. A second detector is affixed to a first end of the second catch optic cable, the second detector provides a second output signal that is representative of light intensity at the $H_2O$ absorption region. A processor is coupled to the first and the second detectors, the processor is configured to determine the concentration of $CO_2$ as a function of the first and the second output signals.

In another exemplary embodiment, the processor is configured to normalize the first output signal using a baseline established as a function of the zero absorption region and to determine the $CO_2$ concentration as a function of the normalized signal and a temperature derived from the second output signal.

In yet another exemplary embodiment, the first laser light source has a sweep range centered at about 2.7082 μm and said second laser light source is centered at about 1388.8 nm.

In yet another exemplary embodiment, the first laser has a sweep range including substantially zero absorption regions on opposite sides of said $CO_2$ absorption feature.

In yet another exemplary embodiment, the first laser light source has a sweep range from about 2.7064 μm to about 2.7069 μm.

In yet another example, a probe for sampling a fluid stream is disclosed. A tubular housing 40 includes a sampling end and an opposite detecting end. The housing 40 includes a body that defines at least one flow cell at the sampling end. A mirror is disposed in the housing 40 at the sampling end. The mirror has a reflective surface facing the detecting end. A lens is disposed in the housing 40 between the mirror and the detecting end. A window is disposed in the housing 40 between the lens and the detecting end. A collet is disposed in the housing 40 between the window and the detecting end. The collet has an outer wall that defines a counter bore open to the detecting end, a plurality of raceways and a keyway. A first insert is disposed in said collet bore. The first insert has a plurality of matching raceways and a key for engaging with the keyway. A second insert is disposed in the collet bore between the first insert and the detecting end. The second insert has a plurality of matching raceways and a key for engaging with the keyway. A pitch hollow wave guide is disposed within one of the plurality of raceways in the inserts and the collet. The pitch hollow wave guide exits the housing 40 at the detecting end. A catch hollow wave guide is disposed within one of the plurality of raceways in the inserts and the collet. The catch hollow wave guide exits the housing 40 at the detecting end. A pitch optical fiber is disposed within one of the plurality of raceways in the inserts and the collet. The pitch optical fiber exists the housing 40 at the detecting end. A catch optical fiber is disposed within one of the plurality of raceways in the inserts and the collet. The catch optical fiber exits the housing 40 at the detecting end. An inner tube is disposed in the housing 40 between the second insert and the detecting end. The inner tube surrounds the hollow wave guides and the optical fibers. The inner tube has male threads for engaging with a matching set of female threads inside the housing 40 such that the inner tube can retract into or extend out of the housing 40 with a turning motion. When the inner tube is turned in one direction in relation to the housing 40, the inner tube retracts into the housing 40, causing the first insert to grip the hollow wave guides and the optical fibers such that they are fixed in place with respect to the lens. By fixing the hollow wave guides and optical fibers in place, the correct optics for the probe are maintained even as the probe is subjected to the vibrations and harmonics of a running engine.

In yet another example, a first spacer is disposed in the housing 40 between the mirror and the lens and a second spacer is disposed in the housing 40 between the lens and the window.

In yet another example, a seal is disposed in the housing 40 between the window and the collet.

In yet another example, the first insert is made of an elastomeric material.

In yet another example, the elastomeric material has a Shore durometer of between approximately 70 A-90 A.

In yet another example, the at least one flow cell is disposed between the mirror and the window.

In yet another example, one of the at least one flow cells is disposed between the mirror and the lens and another one of the at least one flow cells is disposed between the lens and the window.

In yet another example, each of the at least one flow cells is configured to sample a fluid stream that is flowing in a direction that is substantially parallel to a longitudinal axis of the housing 40.

In yet another example, each of the at least one flow cells is configured to sample a fluid stream that is flowing in a direction that is substantially perpendicular to a longitudinal axis of the housing 40.

In yet another example, a method for determining a concentration of CO2 in a complex fluid stream is disclosed. In this example, the following steps are performed: a) providing a probe with a sampling chamber; b) providing a swept-k laser having a sweep range including a significant absorption feature of $CO_2$ and at least one substantially zero absorption region; c) providing a diode laser having a frequency of a significant absorption feature of $H_2O$; d) producing light beams with the lasers; e) directing the light beams into the probe and through the sampling chamber, the sampling chamber containing the complex fluid stream to be sampled; f) receiving the light beams at separate detectors, the detectors producing output signals representative of light intensities in the light beams; and g) determining the concentration of $CO_2$ with a processor as a function of the output signals of the two detectors.

In another example, the method further includes the step of normalizing at least one of the output signals with a processor as a function of light intensity in the zero absorption region. The normalizing step occurring prior to the determining step.

In another example, the method further includes the step of correcting the output signal with a processor as a function of $H_2O$ concentration. The correcting step occurs after the normalizing step and before the determining step.

These and other objects, advantages, and features will be more fully understood and appreciated by reference to the detailed description of the current embodiment and the drawings.

DETAILED DESCRIPTION

As summarized above, an exemplary probe is described in connection with the measurement of $CO_2$ concentrations within an engine intake manifold 20. While an intake manifold 20 is used in the present examples, it is to be understood that the exemplary probes may also be used in an exhaust manifold, in an EGR line or in other areas of an internal combustion engine as well as other applications.

Figure 4:
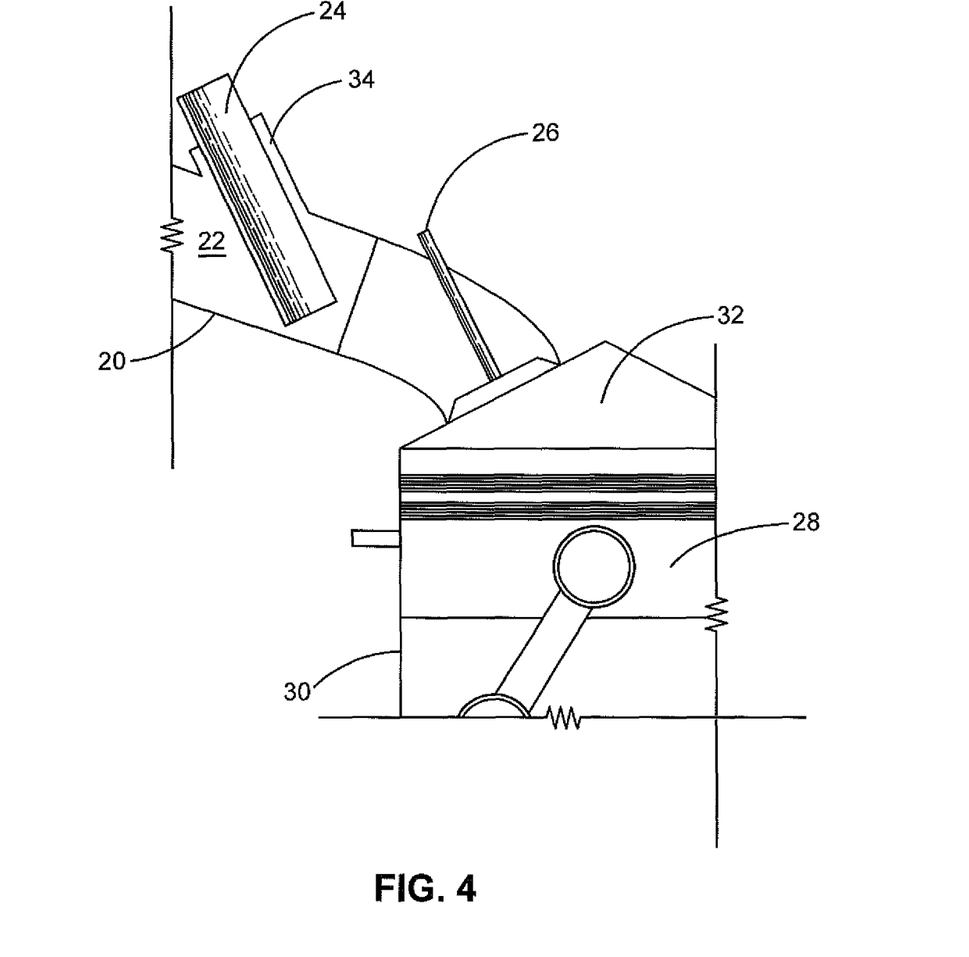
FIG. 4 is a schematic sectional view of an exemplary probe installed in an intake manifold.

FIG. 4 shows an exemplary runner portion 22 of an engine intake manifold 20 and an exemplary probe 24 located upstream of an intake valve 26. A piston 28 reciprocates inside a cylinder 30 to define a combustion chamber 32 above the piston 28. Ports 34 defined by the intake manifold 20 receive the probe 24 and may be machined pads cast into the manifold 20 during the manufacturing process or may be pads welded in place after manufacturing the manifold 20. In this embodiment, the probe 24 is mounted to the intake manifold 20 via a standard bore-through SwageLok tube union boss, and positioned via a nonswaging ferrule. The probe 24 may be mounted using other hardware, if desired. In this general configuration, the probe 24 is able to sample $CO_2$ and $H_2O$ concentrations from relatively cool EGR and relatively hot backflow sources.

Figure 5:
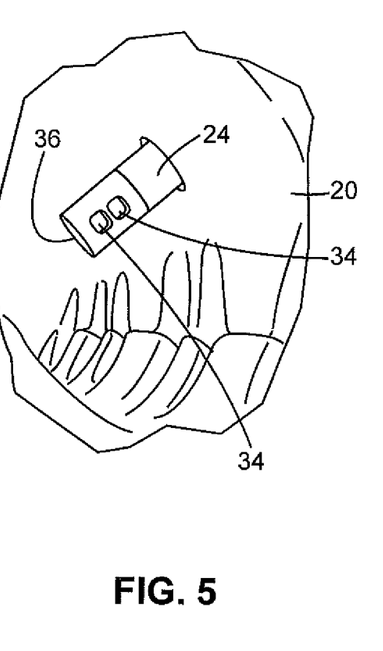
FIG. 5 is another schematic view of an exemplary probe installed in an intake manifold.

FIG. 5 shows an exemplary probe 24 mounted in an intake manifold 20. As can be seen, a sampling end 36 of the probe 24 may be angularly positioned so that one or more flow cells 38 are located at the location and in the direction where samples are to be taken. Again, although shown with respect to an intake manifold 20, the probe 24 may be installed in essentially any other structure containing a fluid stream, such as an exhaust manifold or exhaust gas recycling line for example.

Figure 6:
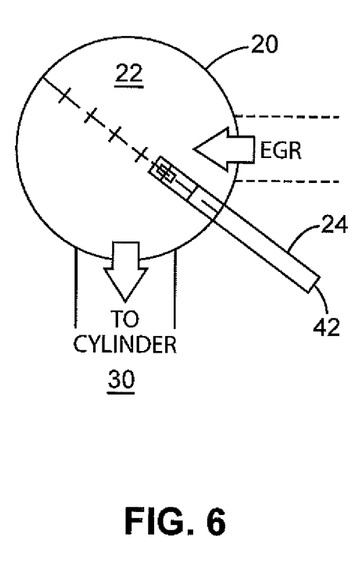
FIG. 6 is yet another schematic view of an exemplary probe installed in an intake manifold.

Referring to FIG. 6, a schematic representation of a probe 24 installed in an intake manifold 20 is illustrated. In this example, the probe 24 may be traversed into and out of the intake manifold 20 to spatially map $CO_2$ concentrations across the intake runner 22. This provides an enhanced diagnostic for understanding the actual conditions around the intake valve 26 spatially and temporally while an engine is running.

Figure 7:
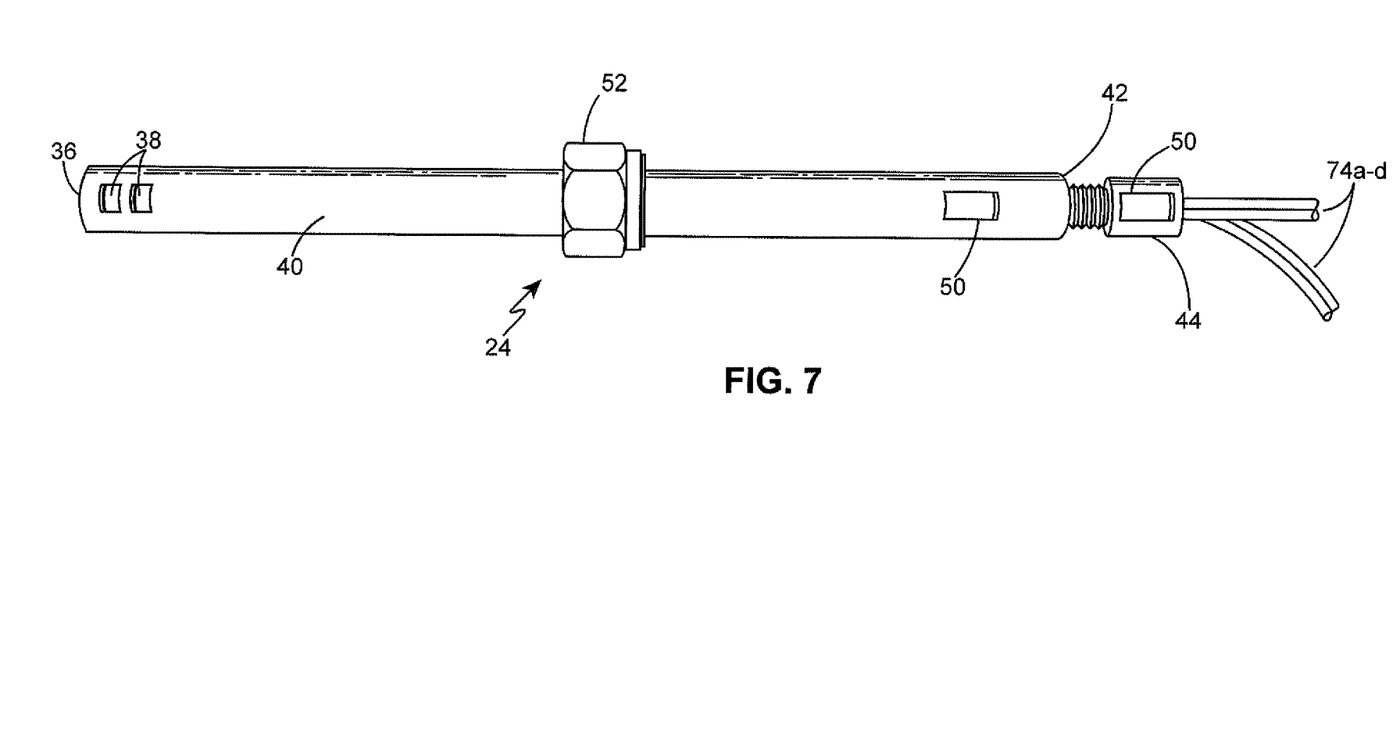
FIG. 7 is an external view of an exemplary probe.

Referring to FIG. 7, the major external features of an exemplary probe 24 will now be described. A tubular-shaped housing 40 includes a sampling end 36, an opposite detecting end 42, and defines at least one flow cell 38 at the sampling end 36. The housing 40 may be made of corrosion and oxidation-resistant, high temperature capability material such as stainless steel for example. In this example, the housing 40 is made of 0.375 inch (9.5 mm) diameter stainless steel tubing but may be otherwise sized and shaped. An inner tube 44 includes external threads 46 that engage with internal threads 48 in the housing 40 (see FIG. 8). Machined flats 50 allow the inner tube 44 to be rotated about its longitudinal axis in relation to the housing 40 using tools. This angular rotation causes the inner tube 44 to retract into or extend out of the housing 40 while the threads 46, 48 engage. The significance of this movement will be described in greater detail later. Probe fastening means 52, such as a nut and ferrule, may be fit around the housing 40 for securing the probe 24 in a threaded aperture as described above. For example, the fastening means 52 may be a SWAGELOCK brand nut. In some examples, the fastening means is moveable along the longitudinal length of the probe 24, allowing the probe 24 to be translated spatially and angularly within the fluid path being sampled.

Figure 8:
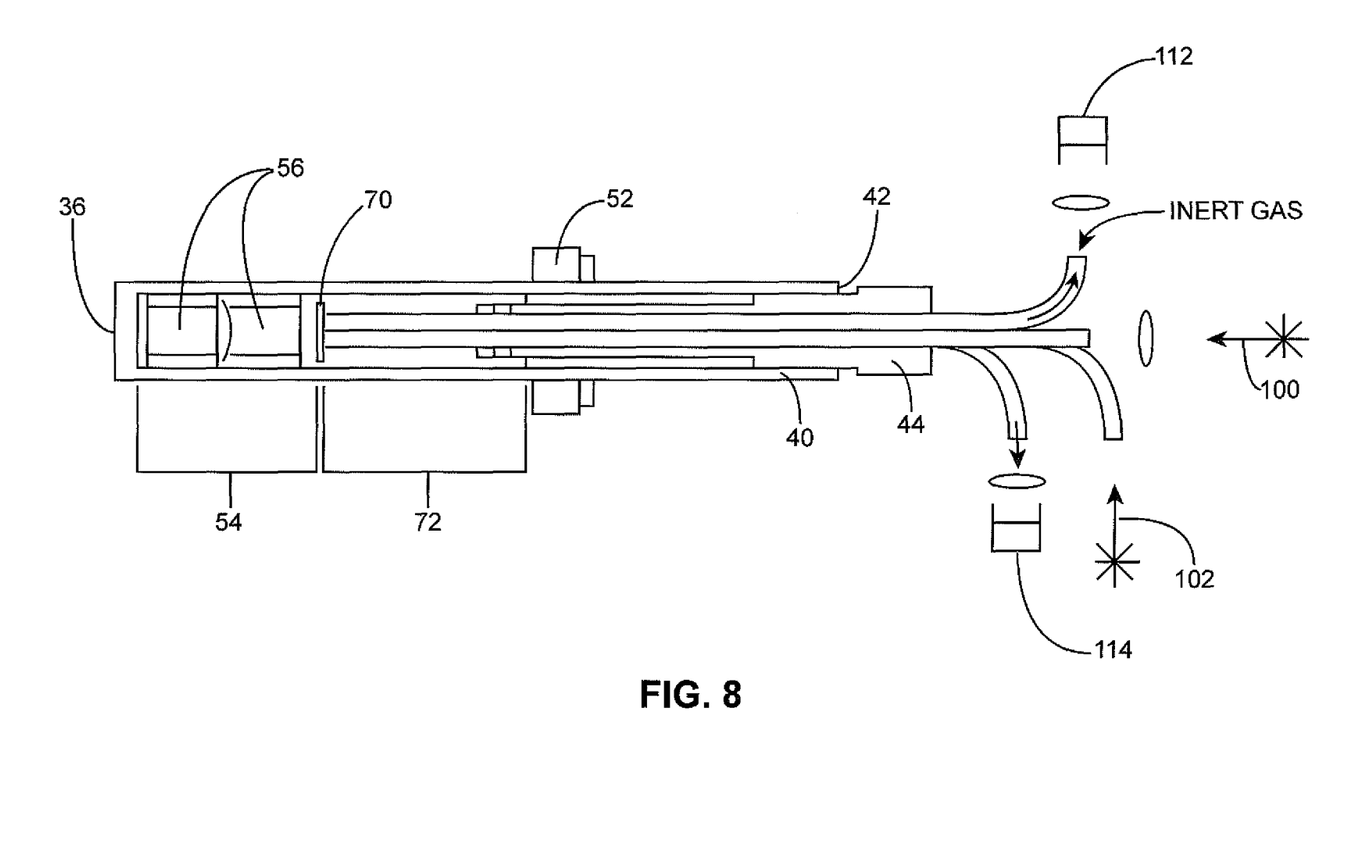
FIG. 8 is a longitudinal sectional view of an exemplary probe illustrating the various elements as assembled.
Figure 9:
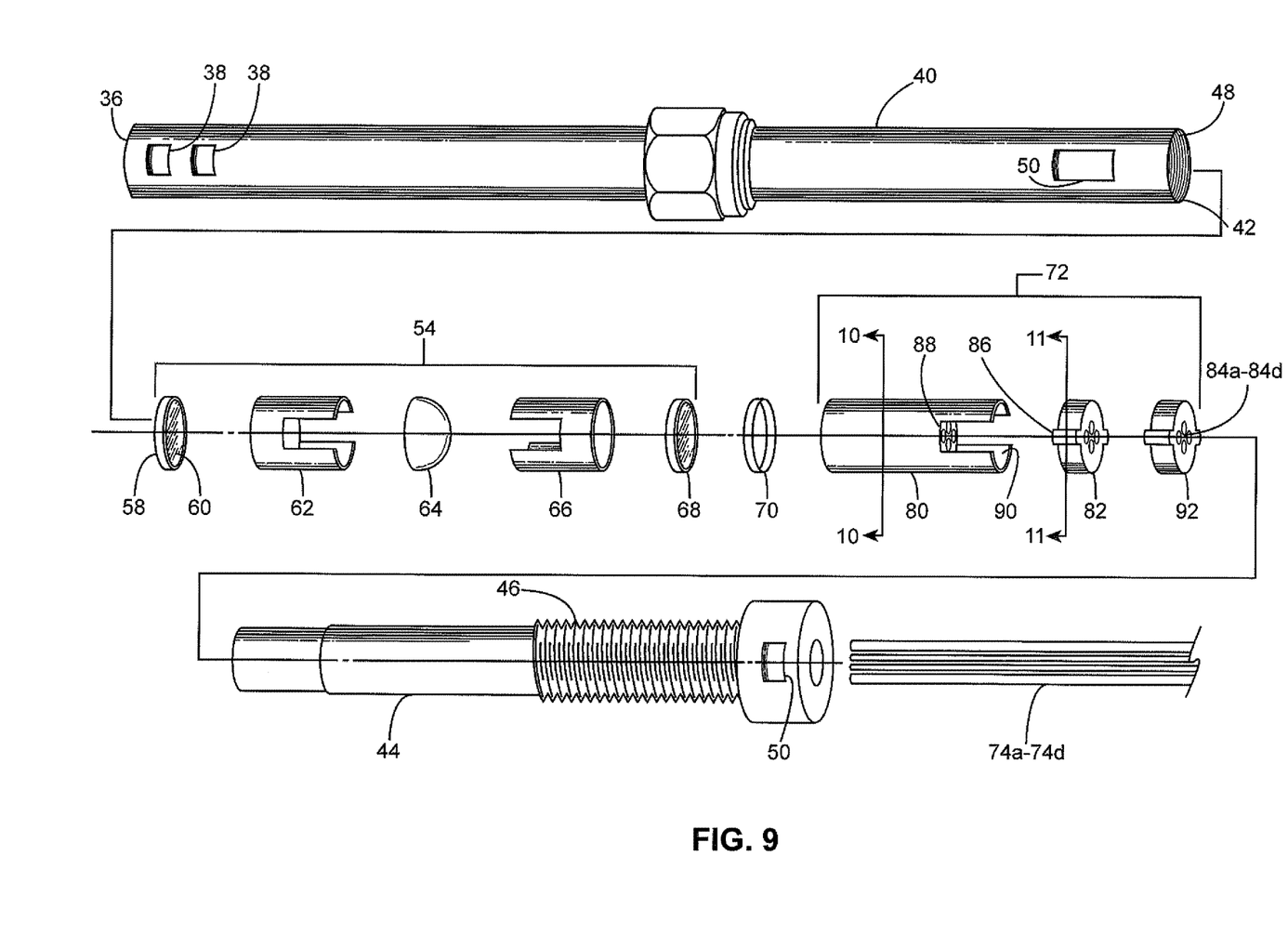
FIG. 9 is an exploded view illustrating the various elements of the assembly.

With reference now to FIGS. 8 & 9, the major internal features of an exemplary probe 24 will now be fully described. As earlier described, a tubular housing 40 defines at least one flow cell 38 proximate the sampling end 36. The internal components and other features will now be described from the sampling end 36 to the detecting end 42.

An optics assembly 54 focuses one or more light sources across the sampling area 56 within the flow cell 38 and includes several individual elements. A minor 58 is disposed inside of the housing 40 at the sampling end 36 and includes a reflective surface 60 that faces the detecting end 42. A first spacer 62 is disposed inside of the housing 40 between the mirror 58 and the detecting end 42. A lens 64 is disposed inside of the housing 40 between the first spacer 62 and the detecting end 42. A second spacer 66 is disposed inside of the housing 40 between the lens 64 and the detecting end 42. The first and second spacers 62, 66 accurately locate and secure the lens 64 at the appropriate focal length from the reflective surface 60 of the mirror 58. A window 68 is disposed inside of the housing 40 between the second spacer 66 and the detecting end 42. Note that when the probe 24 is assembled, the fluid sampling areas 56 are disposed between the mirror 58 and the lens 64 and the lens 64 and the window 68.

A seal 70 may be disposed inside the housing 40 between the window 68 and the detecting end 42. The seal 70 is made of a high temperature elastomeric material and compresses under load to prevent leakage of an inert gas fluid inside the probe 24. The seal 70 isolates an optical cable alignment assembly 72 from atmospheric $CO_2$ and a more complete description of its function will be provided in detail later.

The optical cable alignment assembly 72 ensures that optical cables 74a, 74b, 74c, 74d are properly aligned with and positioned in relation to the optics assembly 54. Each of the optical cables 74a, 74b, 74c, 74d includes a first end 76 and a second end 78. A collet 80 includes an outer wall that defines a counter bore 90, a plurality of raceways 84a, 84b, 84c, 84d, and at least one keyway 88. The collet 80 is disposed inside of the housing 40 between the window 68 and the detecting end 42 and, when a seal 70 is installed against the window 68, the collet 80 is disposed inside of the housing 40 between the seal 70 and the detecting end 42. The collet 80 is made of a corrosion and oxidation-resistant, high temperature capability material such as stainless steel for example. A first insert 82 includes a plurality of raceways 84a, 84b, 84c, 84d that generally match and align with the raceways 84a, 84b, 84c, 84d in the collet 80 and a protruding key 86 for engaging the keyway 88 in the collet 80. The first insert 82 is disposed inside of the counter bore 90 of the collet 80 and is made from a high temperature elastomeric material that will deflect under load. In one example, the first insert 82 is made from an elastomer material having a Shore durometer of between approximately 70 A-90 A. In another example, the first insert 82 is made from an elastomer material having a Shore durometer of approximately 80 A. A second insert 92 includes a plurality of raceways 84a, 84b, 84c, 84d that generally match and align with the raceways 84a, 84b, 84c, 84d in the collet 80 and the first spacer 62 and a protruding key 86 for engaging the keyway 88 in the collet 80. The second insert 92 is disposed inside of the counter bore 90 of the collet 80 between the first insert 82 and the detecting end 42 and is made of a corrosion and oxidation-resistant, high temperature capability material such as stainless steel for example.

An inner tube 44 is disposed inside of the housing 40 and defines a central aperture 94 that extends from a load application end 96 to a torque accepting end 98. A set of external threads 46 cooperate with a matching set of internal threads 48 in the housing 40 such that the inner tube 44 can retract into or extend out of the housing 40 with a turning motion. The load application end 96 contacts and applies a force against the second insert 92 as the inner tube 44 retracts into the housing 40 with a turning action at the torque accepting end 98.

Optical cables 74a, 74b, 74c, 74d pass through the central aperture 94 in the inner tube 44, through the matching raceways 84a, 84b, 84c, 84d, in the second insert 92, the first insert 82, and the collet 80. Note that the raceways 84a, 84b, 84c, 84d are slightly oversized to provide a slight clearance with the optical cables 74a, 74b, 74c, 74d during assembly. When assembled, the ends of the optical cables 74a, 74b, 74c, 74d may extend beyond the end of the collet 80, may be flush with the end of the collet 80, or may recede slightly into the collet 80.

The following dimensions are exemplary in nature and it is to be understood that other sizes may function better for a particular application. Optical cable 74a is also known as a pitch hollow wave guide and projects a laser light from a first laser light source 100 (FIG. 13). Hollow waveguides may provide improved light transmission as compared to other types of optical fibers or light guides. Optical cable 74a is 0.85 mm+/−0.03 mm diameter and fits within a 0.88 mm diameter raceway 84a. Optical cable 74b is also known as a catch hollow wave guide and catches the first laser light reflected from the reflective surface 60 of the minor 58 and directed by the lens 64. Optical cable 74b in this example is 1.6 mm+/−0.05 mm diameter and fits within a 1.66 mm+/−0.2 mm diameter raceway 84b. Optical cable 74c is also known as a pitch optical fiber and projects a laser light from a second laser light source 102. Optical cable 74c is 0.8 mm+0.05 mm−0.0 mm diameter and fits within a 0.86 mm diameter raceway 84c. Optical cable 74d is also known as a catch optical fiber and catches the second laser light reflected from the reflective surface 60 of the mirror 58 and directed by the lens 64. The catch optical cable 74d in this example is 1.04 mm+/−0.03 mm diameter and fits within a 1.08 mm diameter raceway 84d.

To assemble the probe 24, the optics assembly 54 is first inserted into the housing 40 at the detecting end 42 and seated against the sampling end 36. Next, the seal 70 is inserted and seated against the window 68. The optical cables 74a, 74b, 74c, 74d, are next inserted into the central bore 94 of the inner tube 44 and then through the matching raceways 84a, 84b, 84c, 84d in the cable alignment assembly 72. The cable alignment assembly 72, the inner tube 44, and the optical cables 74a, 74b, 74c, 74d, are then inserted into the housing 40 through the detecting end 42. The inner tube 44 is turned with a tool, such as a wench, while the housing 40 is secured with another tool, such as a wrench. The engaged threads 46, 48 cause the inner tube 44 to retract into the outer housing 40, which produces a force against the second insert 92. The second insert 92, in turn, produces a force against the first insert 82, which deforms slightly, due to its elastomeric material. The raceways 84a, 84b, 84c, 84d in the first insert 82 compress slightly and grip the optical cables 74a, 74b, 74c, 74d, securing them in place. Note that the first and second inserts 82, 92 cannot rotate within the collet 80 due to their keys 86 being engaged with keyway 88.

Figure 10:
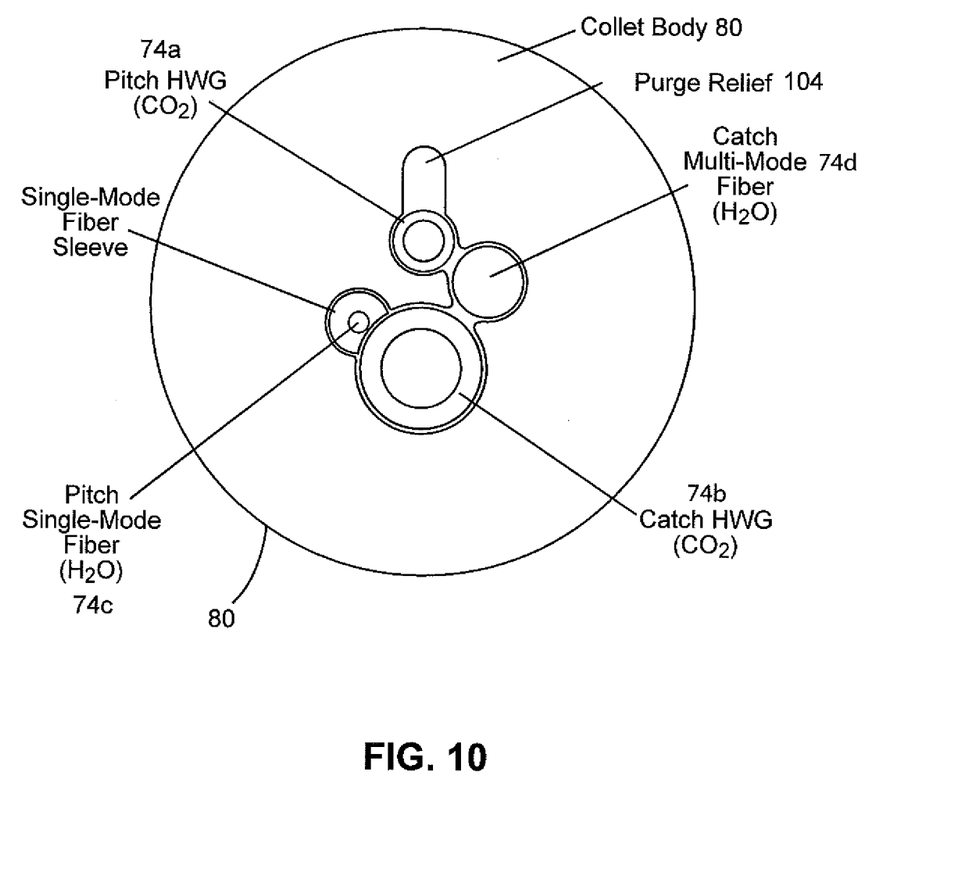
FIG. 10 is a sectional view taken along line 10-10 of FIG. 9 illustrating an exemplary collet and further illustrating the pitch and catch optics layout.
Figure 11:
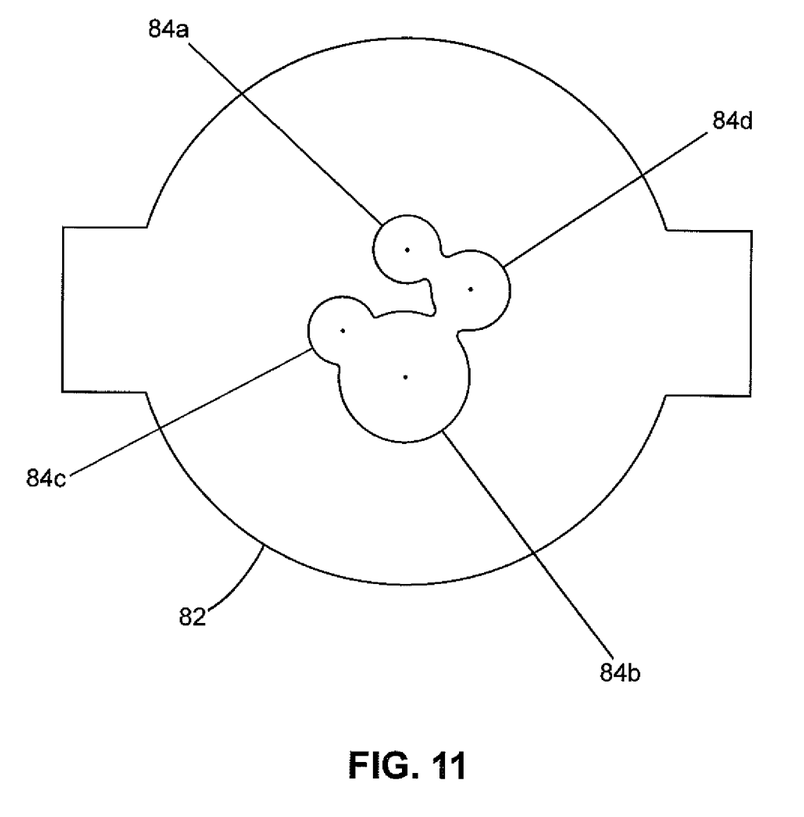
FIG. 11 is a sectional view taken along line 11-11 of FIG. 9 illustrating an exemplary insert.

Referring now to FIGS. 10-11, exemplary raceways 84a, 84b, 84c, 84d, in the collet 80 and first insert 82 are shown. In some examples, a purge relief 104 is also included to allow the introduction or removal of an inert gas, such as nitrogen for example, into or from the detecting end 42 of the probe 24. In other examples, an inert gas is introduced through one of the hollow wave guide optical cables, 74a, 74b. It was found that atmospheric $CO_2$ may be present in the hollow wave guides 74a, 74b, in the area disposed between the window 68 and the collet 80, and around the laser light sources 100, 102 themselves. An inert gas, such as nitrogen for example, may be introduced into: a) an enclosure 106 that surrounds the system 108 as illustrated in FIG. 13; b) the pitch and/or catch hollow wave guide 74a, 74b; c) the purge relief; or, d) combinations of the locations.

Figure 12:
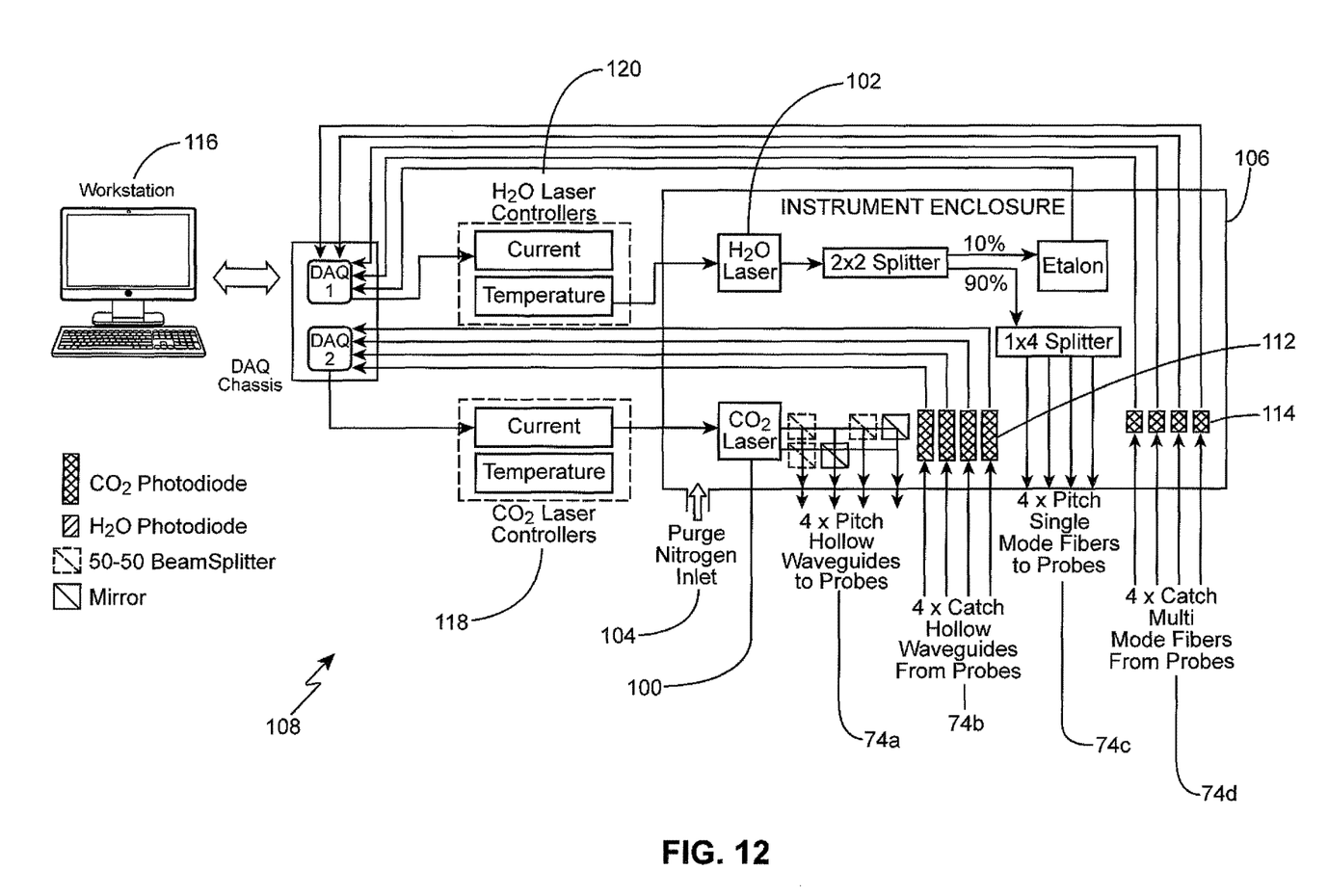
FIG. 12 is a simplified schematic view of an exemplary system for determining the concentration of $CO_2$ in a fluid stream.

A system 108 in accordance with an exemplary embodiment is schematically shown in FIG. 12. The diagnostic system 108 may be disposed in an enclosure 106 for atmospheric $CO_2$ isolation. The diagnostic system 108 of this embodiment permits accurate measurement of $CO_2$ concentrations at various temperatures, and potentially other substances, within a fluid stream using absorption spectroscopy. The system 108 may be used to measure $CO_2$ concentrations in essentially any application. In the illustrated embodiment, the diagnostic system 108 is used to measure $CO_2$ concentrations within an engine intake manifold 20 to determine the spatial and temporal non-uniformities of $CO_2$ in the fluid stream. For example, the system 108 may be used to measure cylinder-to-cylinder and cycle-to-cycle EGR fluctuations. In the context of engines with exhaust gas redistribution (EGR), the diagnostic system 10 may be used to quantify intake EGR fluctuations using $CO_2$ measurements. In some examples, the complex flow behind the intake valve and including both hot and cold exhaust gas constituents may be measured.

The data collected by the diagnostic system 108 may be used to refine the EGR system, the intake manifold 20 shape and distribution characteristics, engine control parameters or other characteristics to improve performance of the engine and minimize $NO_x$ production. Although disclosed in the context of an EGR diagnostic system, the present system may be readily adapted for use in other types of diagnostics. For example, the system 108 may allow diagnostics relating to other engine characteristics that can be assessed using $CO_2$ concentration. The diagnostic system 108 may also be used for applications that do not involve engines. The system may be modified to measure substances other than $CO_2$. For example, the light source, detector and processor may be modified to measure other substances, and provide diagnostics based on those substances can be performed.

The diagnostic system 108 generally includes in connected series a first laser light source 100, a first pitch optical cable 74a, a first catch optical cable 74b and a first detector 112. Note that four probes and eight detectors are used in this particular example to allow measurements in four locations. Also included in connected series is a second laser light source 102, a second pitch optical cable 74c, a second catch optical cable 74d and a second detector 114. The first and second detectors 112, 114 are connected to a processor 116 for determining $CO_2$ concentration based on the output of the two detectors 112, 114.

The laser light sources 100, 102 may be used for a single probe 24 or for a plurality of probes by multiplexing as illustrated. Regardless of the number of probes, the laser-based diagnostic system 108 may be used in connection with a variety of different measurement and analysis methods.

The first laser light source 100 may be essentially any type of laser capable of providing sufficient output over the desired frequency range. In the present embodiments, the laser is a swept-λ laser capable of producing light output over a defined sweep range. In operation, the first laser light source 100 may continuously and repeatedly sweep through a desired frequency range. The sweep range may vary from application to application. In the illustrated embodiment, the laser is configured to measure $CO_2$ concentration in the intake manifold of an engine. In this context, the sweep range of the laser is selected to include a distinctive $CO_2$ absorption region that has high line strength. Further, to assist in normalizing the measurements to a baseline, the sweep range is also selected to include zero absorption regions on opposite sides of the $CO_2$ absorption region. The term "zero absorption region" is used to refer to a region with sufficiently low absorption that it can be used in determining a baseline for normalizing measurements, and is not limited to regions in which there is absolutely no absorption. The sweep range may also be selected to avoid regions that include significant water vapor absorption or absorption from other source of interference. In one example, a wavelength for a range of 2.706 μm to 2.709 μm, centered at about 2.7082 μm, is chosen. The diagnostic system may include a 2.7 μm laser light source having a sweep range centered at about 2.7082 μm. To include the zero absorption regions, the sweep range may be from about 2.7064 μm to about 2.7069 μm. This sweep range is exemplary and the light source may implement other sweep ranges from application to application.

First light source 100 is driven by a first laser controller 118 that is, in turn, controlled by the processor 116. The second laser light source 102 may be a diode laser that is centered about a wavelength of 1388.2 nm. The diode laser is driven by a laser diode controller 120 that is, in turn, controlled by the processor 116. This second light source 102 is used for determining the concentration of $H_2O$ vapor which, in turn, is used to determine temperature. The second laser light source 102 is further described in the incorporated Journal Articles.

The measurements produced by the detectors 112, 114 are processed by processor 116 to determine the concentration of $CO_2$. This process may include the steps of: (a) determining the zero absorption regions; (b) normalizing the output signal using a baseline established as a function of the zero absorption regions; and, (c) determining the $CO_2$ concentration from the normalized output signal and the temperature derived from the $H_2O$ vapor concentration measurement. Once the signal component has been normalized, the $CO_2$ concentration may be determined along with temperature using conventional absorption spectroscopy methodologies, which will not be described in detail here.

The method of this embodiment also generally includes the steps of, for each pass through the sweep range, (i) collecting data from the detector, (ii) fitting the baseline to the measured data, (iii) subtracting the baseline and fitting a lineshape to the measured data, (iv) determining the concentration from the lineshape, and (v) incorporating the concentration into a plot showing $CO_2$ concentration over time and temperature. For example, lower temperatures are indicative of exhaust gas $CO_2$ entering the intake plenum through the EGR system, and higher temperatures are indicative of residual exhaust gas $CO_2$ back flowing past the intake valve and into the intake plenum.

One implementation of this general process will now be described in more detail and is fully described in U.S. application Ser. No. 14/051,788, entitled EGR DISTRIBUTION AND FLUCTUATION PROBE BASED ON CO2 MEASUREMENTS, filed Oct. 11, 2013, and incorporated by reference as noted above. It is noted that the laser undergoes a generally linear increase in intensity from one end of each sweep range to the other end of that sweep range. This general increase in intensity is a practical result of the nature of the first laser light source and it may be desirable to factor out the laser intensity increase, for example, as described below. In this process, the detector 112 measurements associated with a single sweep are analyzed together to produce a single data point. For example, the measurements occurring during the timeframe associated with the first pass through the sweep range of the first laser light source 100 are grouped together and processed to produce a single point. Data from four sequential passes through the sweep range, produces four sequential data points. It should also be noted that because the first laser light source 100 is changing frequency to move through the sweep range over time, there is a correlation between time and first laser light source output frequency in the measured data.

For each collection of data associated with a single data point, the processor 116 analyzes the data to fit the baseline for the measured data. The data can be analyzed to determine the baseline using a variety of computational methods known to those skilled in the art.

Once the baseline has been determined, the processor 116 may subtract the baseline from the measured data to provide normalize data. The processor may then produce one or more lineshapes that fit to the normalized data. In this embodiment, the measured data included three peaks that correspond to a $CO_2$ feature and two auxiliary features. In this embodiment, the processor creates three lineshape—one corresponding to each of the peaks. The lineshapes may be produced using a variety of computational methods known to those skilled in the art.

Once the measured data has been normalized and the lineshape(s) have been determined, the $CO_2$ concentration can be determined based on the lineshape or the normalized data for the $CO_2$ feature. For example, the lineshape or the normalized data may be processed in accordance with the Beer-Lambert Law or other suitable computational methods to determine $CO_2$ concentration. The $CO_2$ concentration can then be incorporated into the plot of $CO_2$ concentration against engine crank angle for example. This allows analysis of the engine through a complete engine cycle (e.g., crank angle range of 0-720 degrees).

In addition to providing $CO_2$ concentration, the normalized data and/or the lineshapes may be analyzed to provide pressure and temperature readings. For example, with regard to pressure, the line width of the $CO_2$ feature may be analyzed in accordance with known methods to provide pressure. As another example, temperature can be determined based on the fit of the normalized data to the lineshape in accordance with known methods.

In another example, the fluid temperature may be determined from the $H_2O$ vapor concentration using the second laser light source 102. The methods and apparatuses are fully described in the following journal articles: Jatana G S, Naik S V, Shaver G M, Lucht R P. High-speed diode laser measurements of temperature and water vapor concentration in the intake manifold of a diesel engine. International Journal of Engine Research October 2014 vol. 15 no. 7 773-788; and Jatana G S, Magee M, Fain D, Sameer V, Shaver G M, Lucht R P. Simultaneous high-speed gas property measurements at the exhaust gas recirculation cooler exit and at the turbocharger inlet of a multicylinder diesel engine using diode-laser-absorption spectroscopy. Applied Optics, vol. 54, issue 5, p. 1220.

As an alternative to measuring spatial uniformity, the probe 24 may measure the $CO_2$ concentrations at a given location over time to determine changes in $CO_2$ concentration during several engine cycles. In this application, the temporal differences may be determined to assess cycle-to-cycle uniformity of the EGR system. A single probe 24 may be used to measure $CO_2$ concentrations at a single location over time, or a plurality of probes 24 may be used to simultaneously measure $CO_2$ concentrations at different locations using a laser multiplex system. As an alternative to cycle-to-cycle measurements, the present embodiment may be used to take measurements at essentially any timescale (e.g. individual valve events, or intra-valve events, or longer term drift or variations). The diagnostic system 108 may be used to perform other types of diagnostics that depend on $CO_2$ concentration or the concentration of other substances that may be measured using the system as well.

The above description is that of exemplary embodiments only. Various alterations and changes can be made without departing from the spirit and broader aspects as defined in the appended claims, which are to be interpreted in accordance with the principles of patent law including the doctrine of equivalents. The technologies described and claimed may be available for licensing in specific fields of use from the Assignee of record.

What is claimed is:

1. A system for determining the concentration of $CO_2$ in a complex fluid stream, the system comprising:
   a first laser light source that is coupled to a first end of a first pitch optic cable, the first laser light source being a swept-$\lambda$ laser configured to produce light output over a sweep range that includes a region having a significant absorption feature of $CO_2$ and at least one region of substantially zero absorption;
   a second laser light source coupled to a first end of a second pitch optic cable, the second laser light source configured to produce light output that includes a region having a significant absorption feature of $H_2O$;
   a lens disposed proximate a second end of each of the first and second pitch optic cables for directing the first and second lights through a sampling chamber to a mirror;
   a first catch optic cable having a second end disposed proximate said lens for receiving light output from said first laser light source that is reflected from said mirror;
   a second catch optic cable having a second end disposed proximate said lens for receiving light output from said second laser light source that is reflected from said mirror;
   a first detector affixed to a first end of said first catch optic cable, said first detector providing a first output signal that is representative of light intensity across said sweep range;
   a second detector affixed to a first end of said second catch optic cable, said second detector providing a second output signal that is representative of light intensity at the $H_2O$ absorption region; and
   a processor coupled to said first and said second detectors, said processor configured to determine the concentration of $CO_2$ as a function of said first and said second output signals.

2. The system of claim 1 wherein said first laser light source has a sweep range centered at about 2.7082 μm and said second laser light source is centered at about 1388.8 nm.

3. The system of claim 2 wherein said first laser light source has a sweep range including substantially zero absorption regions on opposite sides of said $CO_2$ absorption feature.

* * * * *